United States Patent [19]
Hirschman et al.

[11] Patent Number: 6,048,334
[45] Date of Patent: Apr. 11, 2000

[54] SYRINGE, INJECTOR AND INJECTOR SYSTEM

[75] Inventors: Alan D. Hirschman; David M. Reilly, both of Glenshaw, Pa.

[73] Assignee: Medrad, Inc., Indianola, Pa.

[21] Appl. No.: 09/027,481

[22] Filed: Feb. 20, 1998

Related U.S. Application Data

[63] Continuation-in-part of application No. 08/731,341, Oct. 18, 1996.

[51] Int. Cl.[7] .................................................. A61M 37/00
[52] U.S. Cl. ........................... 604/154; 604/224; 604/218
[58] Field of Search ..................................... 604/131, 151, 604/152, 154, 155, 207–211, 181, 187, 218, 224

[56] References Cited

U.S. PATENT DOCUMENTS

| | | |
|---|---|---|
| 3,702,608 | 11/1972 | Tibbs . |
| 3,858,581 | 1/1975 | Kamen . |
| 3,880,163 | 4/1975 | Ritterskamp . |
| 3,993,061 | 11/1976 | O'Leary ................................... 604/152 |
| 4,059,110 | 11/1977 | Wuthrich et al. . |
| 4,592,745 | 6/1986 | Rex et al. ................................ 604/152 |
| 4,639,245 | 1/1987 | Pastrone et al. ........................ 604/152 |
| 4,677,980 | 7/1987 | Reilly et al. . |
| 4,749,109 | 6/1988 | Kamen ..................................... 604/155 |
| 4,865,591 | 9/1989 | Sams ....................................... 604/186 |
| 4,931,041 | 6/1990 | Faeser ..................................... 604/155 |
| 5,383,858 | 1/1995 | Reilly et al. ............................. 604/152 |
| 5,505,709 | 4/1996 | Funderburk et al. ................... 604/155 |

FOREIGN PATENT DOCUMENTS

| | | |
|---|---|---|
| 0064858 A1 | 11/1982 | European Pat. Off. . |
| 0204977 A1 | 12/1986 | European Pat. Off. . |
| 416385 | 10/1910 | France . |
| 3030239 | 2/1982 | Germany . |
| 1338989 | 11/1973 | United Kingdom . |
| 2117249 | 10/1983 | United Kingdom . |
| 8201998 | 6/1982 | WIPO . |

OTHER PUBLICATIONS

Photograph and label relating to plunger extension developed by Molecular Biosystems, Inc., ("MBI"), manufactured by Medrad, Inc.; Lot No. N4601; Ref. No. 92914–T–101; 1990–1991.

"Variable Infusion Injector Operation Manual", Medrad, Inc., AD203–0100–OM–01, Rev. A; 1990–1991.

PCT International Search Report for International Application No. PCT/US 97/17840.

*Primary Examiner*—Corrine McDermott
*Attorney, Agent, or Firm*—Gregory L. Bradley

[57] ABSTRACT

A syringe for use with a powered injector includes an elongated body having an interior surface, a plunger movably mounted in the elongated body for pressurizing the fluid medium, and a plunger extension connected to the plunger and extending rearward from the plunger. The plunger extension includes at least one spine member operable to engage at least one engagement member on the interior surface of the elongated body. The at least one spine member and the at least one engagement member cooperate to prevent relative rotation between the plunger extension and the elongated body.

15 Claims, 16 Drawing Sheets

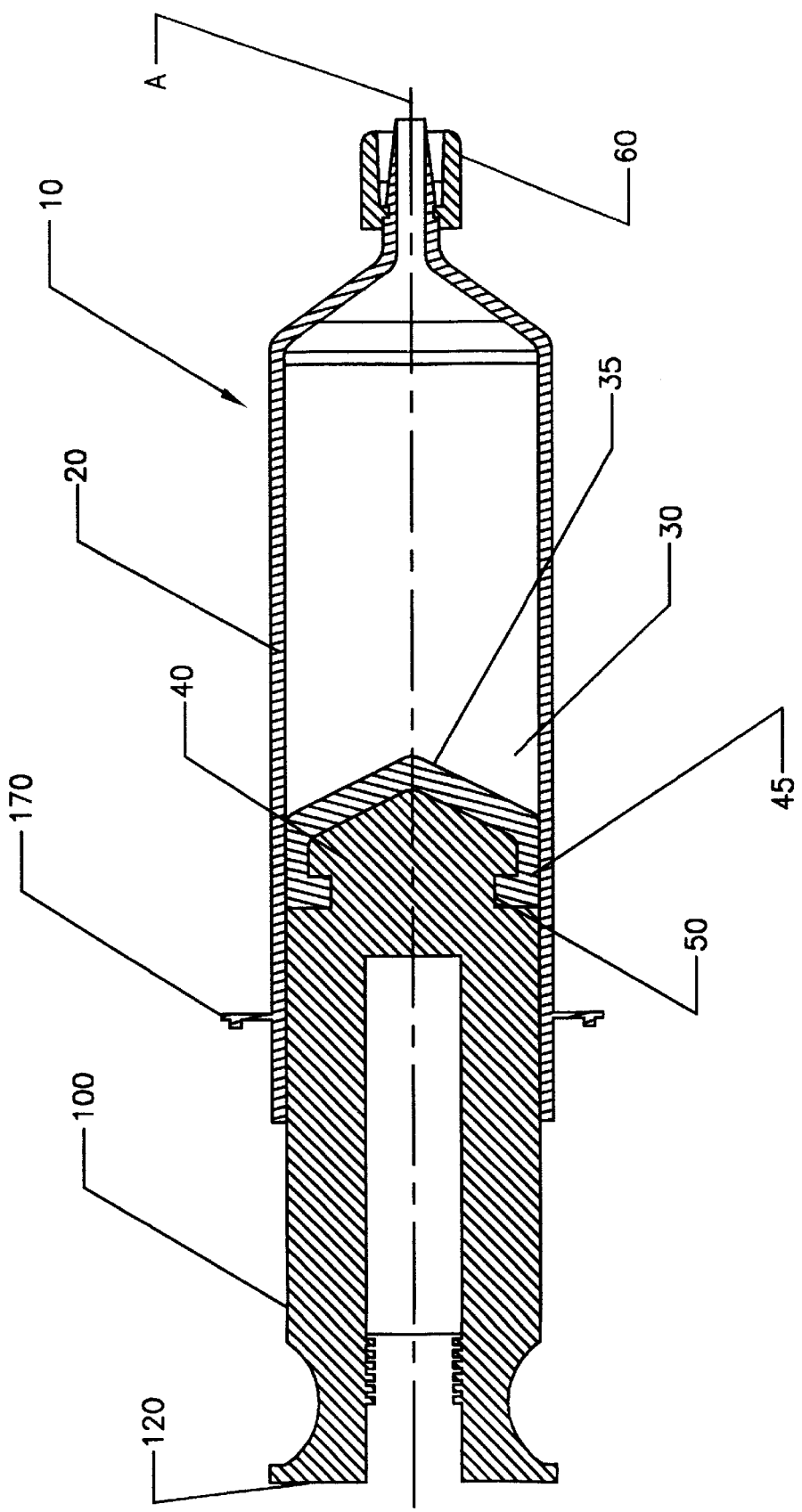

SYRINGE, INJECTOR AND INJECTOR SYSTEM

CROSS-REFERENCE TO RELATED APPLICATION

This application is a continuation-in-part of application Ser. No. 08/731,341, filed on Oct. 18, 1996, the contents of which are hereby incorporated by reference.

FIELD OF THE INVENTION

The present invention relates to a syringe, an injector and an injector system, and, particularly, to a syringe, an injector and an injector system in which the syringe plunger is attachable to a drive member of the injector over a range of relative axial positions.

BACKGROUND OF THE INVENTION

Syringe injection systems have been in use in medical procedures for many years. Many such syringes are operated manually by advancing a plunger extension in operative connection with an internal plunger to pressurize the fluid within the syringe. In numerous medical injection procedures, however, accurate control and/or high pressures are required that cannot be achieved via manual syringe operation. A number of syringes and powered injectors for use therewith have, therefore, been developed for use in medical procedures such as angiography, computer tomography and NMR/MRI. For example, U.S. Pat. No. 5,383,858 discloses a front loading syringe and powered injector in both pressure jacket and jacketless embodiments.

Like syringes operated manually, syringes for use with powered injectors comprise a plunger for forcing the fluid injection medium from the syringe to be injected into the patient. These plungers generally include a cooperating attachment member to enable attachment of the plunger to a powered drive member in the injector. In all cases, there is only one axial position of the injector drive member corresponding to a specific axial position of the plunger at which attachment of the drive member to the plunger is possible. Typically, the plunger must be placed in a single predetermined axial position within the syringe to enable attachment of the plunger to the injector drive member. Often, the predetermined axial position of the plunger is the rearwardmost position.

Such designs present a number of problems. For example, the attachment of the plunger to the drive member is often mechanically difficult for the user, requiring an accurate one-to-one axial alignment. Furthermore, it is preferable to be able to attach the plunger to the drive member when the plunger is not at its rearwardmost position. Attachment of the plunger to the drive member at a somewhat forward position of the plunger, for example, enables the user to draw the plunger back to check for air in the system or to check for blood in the system to ensure proper insertion of an injection needle.

A number of medical procedures also require that the injection media undergo some preparation before powered injection. In some procedures, for example, a contrast medium is received by the end user in the form of a dry powder that must be mixed with a liquid vehicle before injection. In general, the amount of liquid added to a specified amount of dry powder must be relatively precisely measured. Typically, a hand-held or manually operated syringe is used to draw the prescribed amount of water out of a container. This amount of water is then injected into a vial containing the specified amount of the powder. The water and powder are then mixed or agitated before injection into a patient.

For a number of reasons, it is very difficult to inject such a prepared injection medium using current powered injectors. For example, most manually operated syringes, which are typically used to draw the prepared injection medium, cannot be mounted on current powered injectors. Moreover, it is difficult to transfer the medium from a manual syringe into a syringe suitable to be mounted on currently available power injectors. Although a small number of syringes and injectors for use therewith have been developed in which the syringe can be used in a manual mode and in a powered injection mode, for example the syringe/injector system described in WO 82/1988 entitled "Mechanism For Screw Drive And Syringe Plunger Engagement/Disengagement", such syringe/injector systems suffer from the same axial alignment problems discussed above. Further, these prior art syringe/injector systems require the manual alignment of the injector drive mechanism with the syringe plunger.

It is, therefore, desirable to develop a syringe and a powered injector for use therewith which minimize or eliminate the alignment difficulties discussed above. It is also desirable to develop such a syringe and injector in which the syringe can be operated in a manual mode and in a powered injection mode.

SUMMARY OF THE INVENTION

Accordingly, the present invention provides a syringe and a powered injector for use therewith in which the syringe is attachable to a powered drive member of an injector over a range of relative axial positions of the syringe plunger and the drive member. The syringe comprises an elongated body and a plunger movably mounted in the elongated body to pressurize a fluid medium to be injected. The syringe also comprises a plunger extension connected to the plunger and extending rearward from the plunger. In one embodiment, the plunger extension comprises a plurality of plunger attachment members located over a range of axial positions on the plunger extension. Each of the plurality of plunger attachment members is adapted to form a releasable attachment with at least one cooperating injector attachment member on the powered drive member. In another embodiment, the plunger extension of the plunger comprises at least one plunger attachment member which is adapted to form a releasable attachment with each of a plurality of corresponding injector attachment members located over a range of axial positions on the powered drive member. By providing a plurality of cooperating attachment members over a range of axial positions on at least one of the plunger extension or the powered drive member, operative attachment of the plunger and the drive member is made possible at multiple axial positions of the plunger (within the syringe) for each axial position of the drive member over at least a range of possible plunger axial positions. Attachment of the plunger to the drive member at various axial positions of the plunger thus becomes an easier task than previously possible with current powered injector systems.

In another embodiment, the plunger extension preferably comprises a plurality of plunger attachment members located over a range of axial positions on the plunger extension. Each of the plurality of plunger attachment members preferably is adapted to form a releasable attachment with each of a plurality of cooperating injector attachment members located over a range of axial positions on the powered drive member. As with the above-described embodiments, operative attachment of the plunger and the drive member is possible at multiple axial positions of the plunger for each axial position of the drive member over at least a range of possible plunger axial positions. Moreover, providing a plurality of cooperating attachment members on each of the plunger extension and the powered drive member enables cooperating attachment of more than one of the attachment members of the plunger extension with more than one of the attachment members of the powered drive member over a range of relative axial positions of the plunger and the drive member. Such multiple cooperating attachment points provides a stronger connection than provided by a single attachment point and enables use of a wider range of construction materials for the plunger extension and/or the powered drive member. For example, the plunger extension may be fabricated from a disposable plastic material.

Preferably, the attachment members on the plunger extension and the drive member are positioned substantially symmetrically about a common axis to reduce or eliminate uneven loading and torque.

Preferably, the plunger extension is adapted to enable operation of the syringe in a manual mode as well as a powered injection mode. In that regard, the plunger extension preferably extends beyond the rear of the elongated body of the syringe and preferably comprises a flange or pressure member on a rearward end thereof to facilitate manual operation.

BRIEF DESCRIPTION OF THE DRAWINGS

FIG. 1 illustrates in cross-section an embodiment of a syringe of the present invention.

DETAILED DESCRIPTION OF THE INVENTION

Figure 2A:
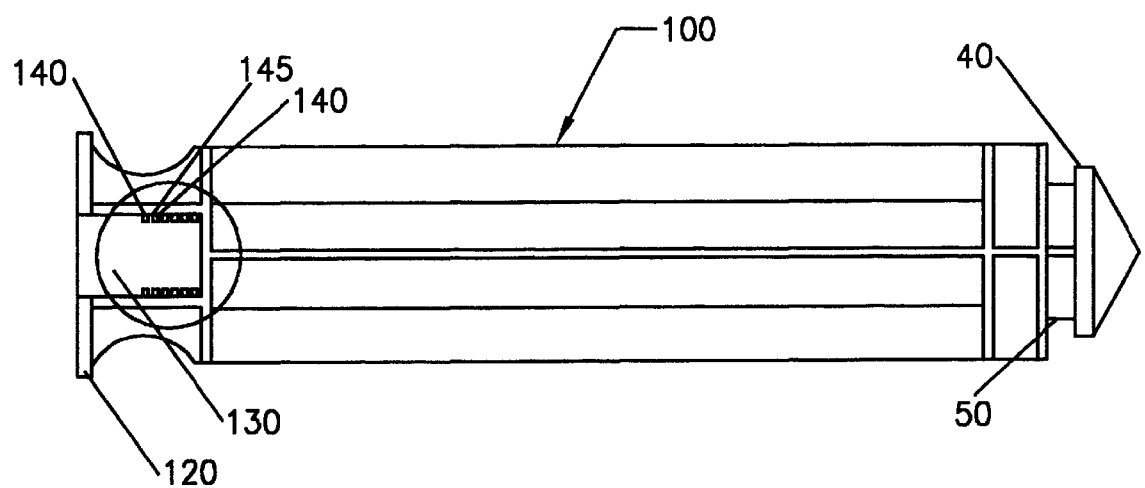
FIG. 2A illustrates an elevation of an embodiment of a plunger base and plunger extension of the present invention.

As illustrated in FIG. 1, syringe 10 comprises an elongated and preferably cylindrical body 20. A plunger 30 is slidably disposed inside cylindrical body 20. Preferably, plunger 30 comprises an elastomeric plunger surface or sealing cover 35 and a base 40. Base 40 is best illustrated in FIGS. 1, 2A, 2C and 2D and is preferably fabricated from a relatively structurally strong material such as a polypropylene, nylon or polycarbonate.

Contact surface 35 fits over and is supported by base 40. As best illustrated in FIG. 1, contact surface 35 may comprise an inwardly projecting circumferential attachment member 45. Attachment member 45 is designed to seat in a channel 50 of base 40 to hold contact surface 35 on base 40. When supported by base 40 and positioned within elongated body 20, the side perimeter of contact surface 35 forms a cylindrical sealing engagement with the inner sidewall of elongated body 20. When drawn rearward, plunger 30 causes fluids to be drawn into elongated cylindrical body 20. When forced forward, plunger 30 causes any fluid within elongated cylindrical body 20 to be forced out of elongated cylindrical body 20 via syringe tip 60.

As used herein to describe syringe 10, the terms "axial" or "axially" refer generally to an axis A around which syringe 10 is preferably formed (although not necessarily symmetrically therearound). The term "radial" refers generally to a direction normal to axis A. The terms "rear" or "rearward" refer generally to an axial direction away from syringe tip 60. The terms "front" or "forward" refer generally to an axial direction toward syringe tip 60.

Syringe 10 also comprises a plunger extension 100 which is operatively connected to plunger 30 and preferably extends rearward from plunger 30 beyond the rear of elongated cylindrical body 20. In the embodiment illustrated in FIGS. 2A through 2D, plunger extension 100 is formed integrally with plunger base 40. Plunger extension 100 may be fabricated, however to be permanently attached or releasably attachable to base 40.

Syringe 10 is preferably designed to be front-loading onto corresponding injector 200. A front-loading syringe and injector system is disclosed in U.S. Pat. No. 5,383,858, the disclosure of which is incorporated herein by reference. The present invention is equally applicable, however, to syringe and injector systems other than front-loading syringe and injector systems.

Figure 3A:
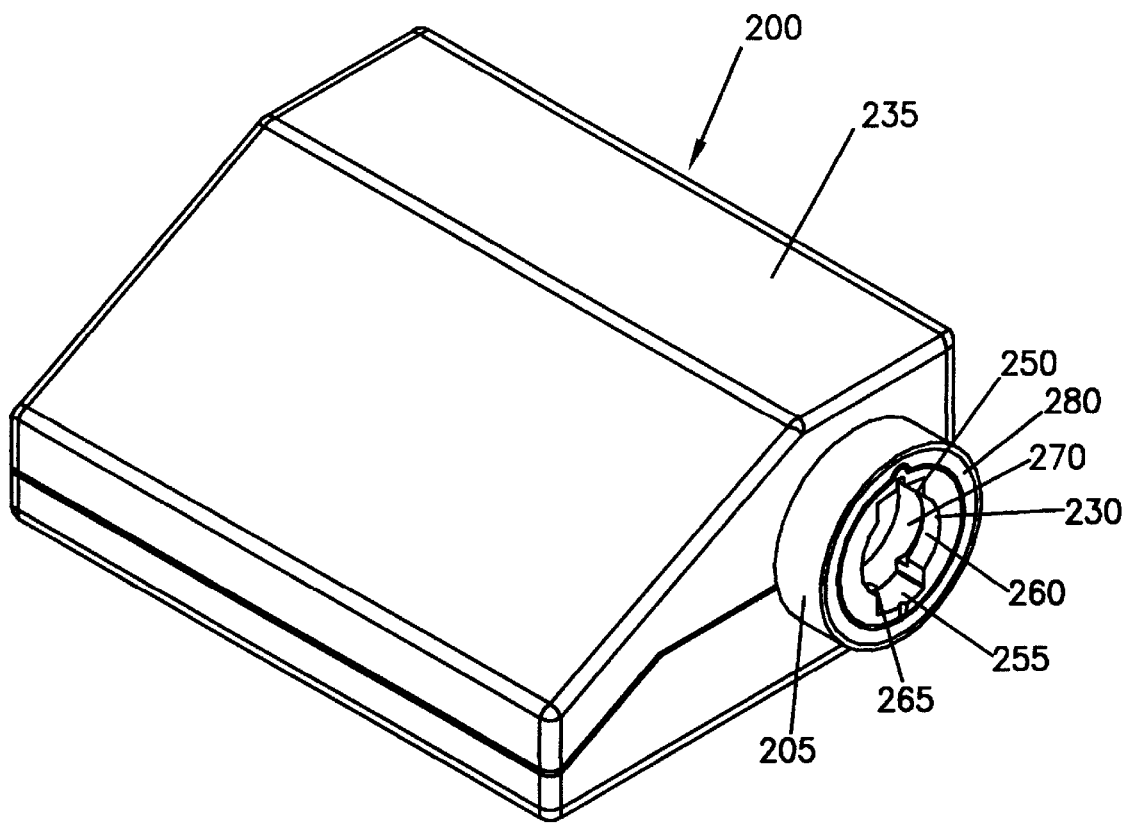
FIG. 3A illustrates a perspective view an embodiment of the powered injector of the present invention.
Figure 3B:
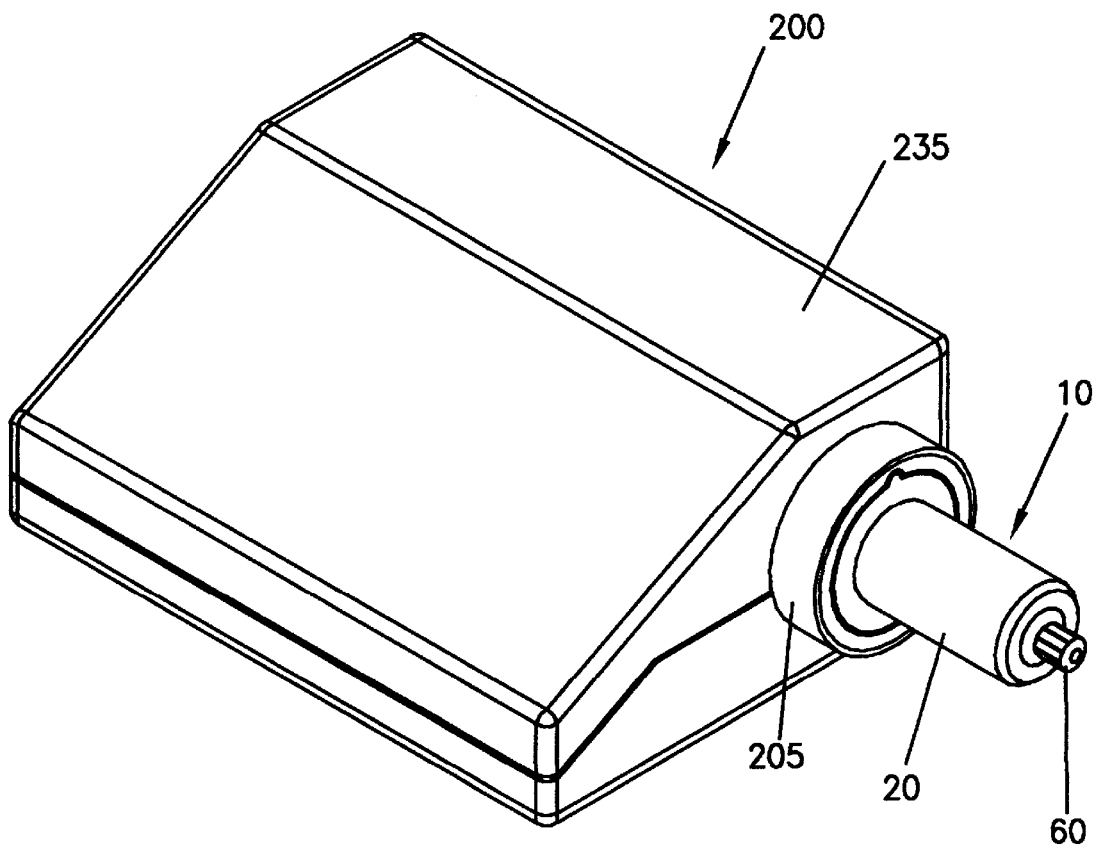
FIG. 3B illustrate a perspective view of the powered injector of FIG. 3A with the syringe mounted thereon.
Figure 3C:
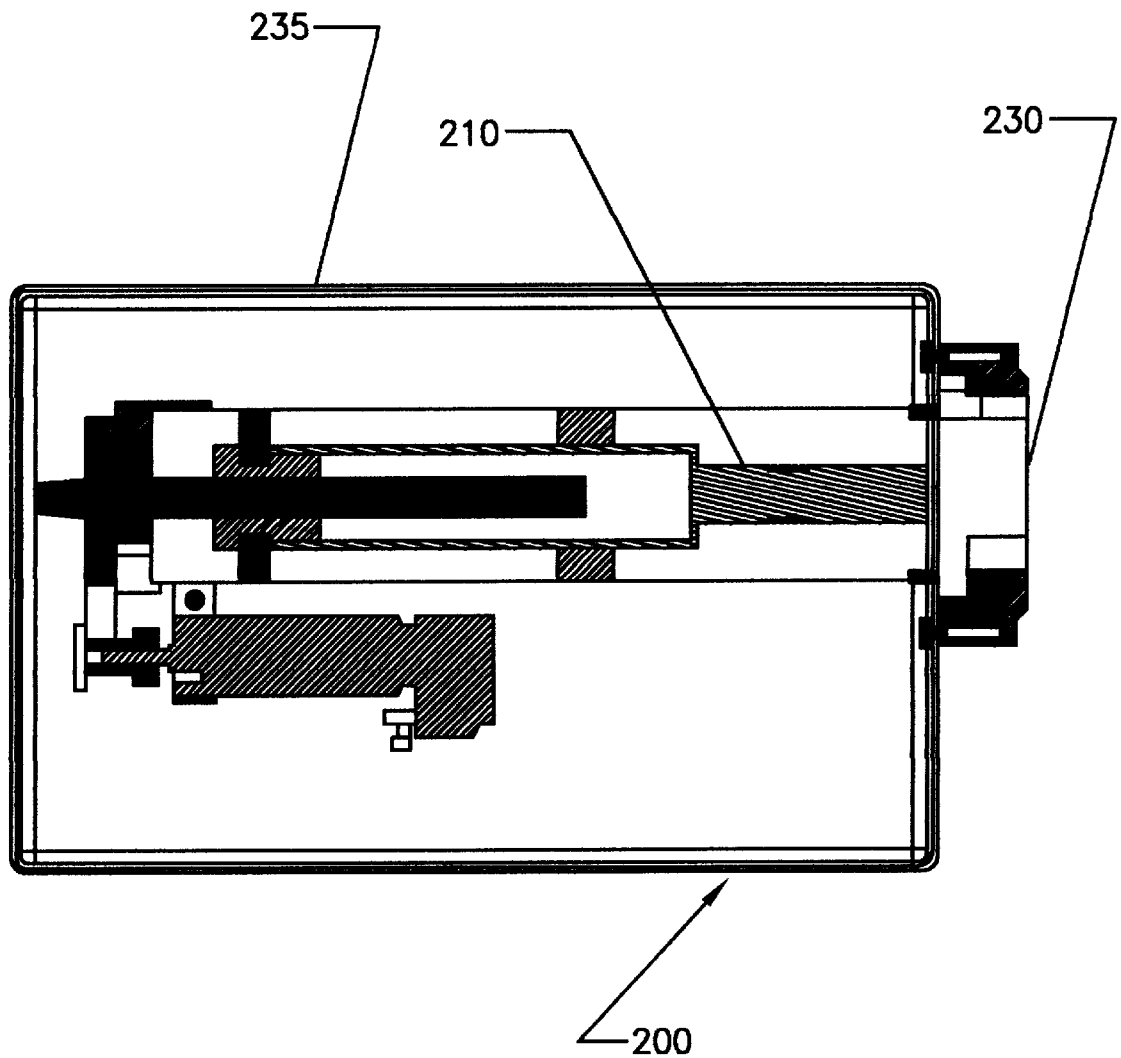
FIG. 3C illustrates a cross-sectional view of the powered injector of FIG. 3A.
Figure 3D:
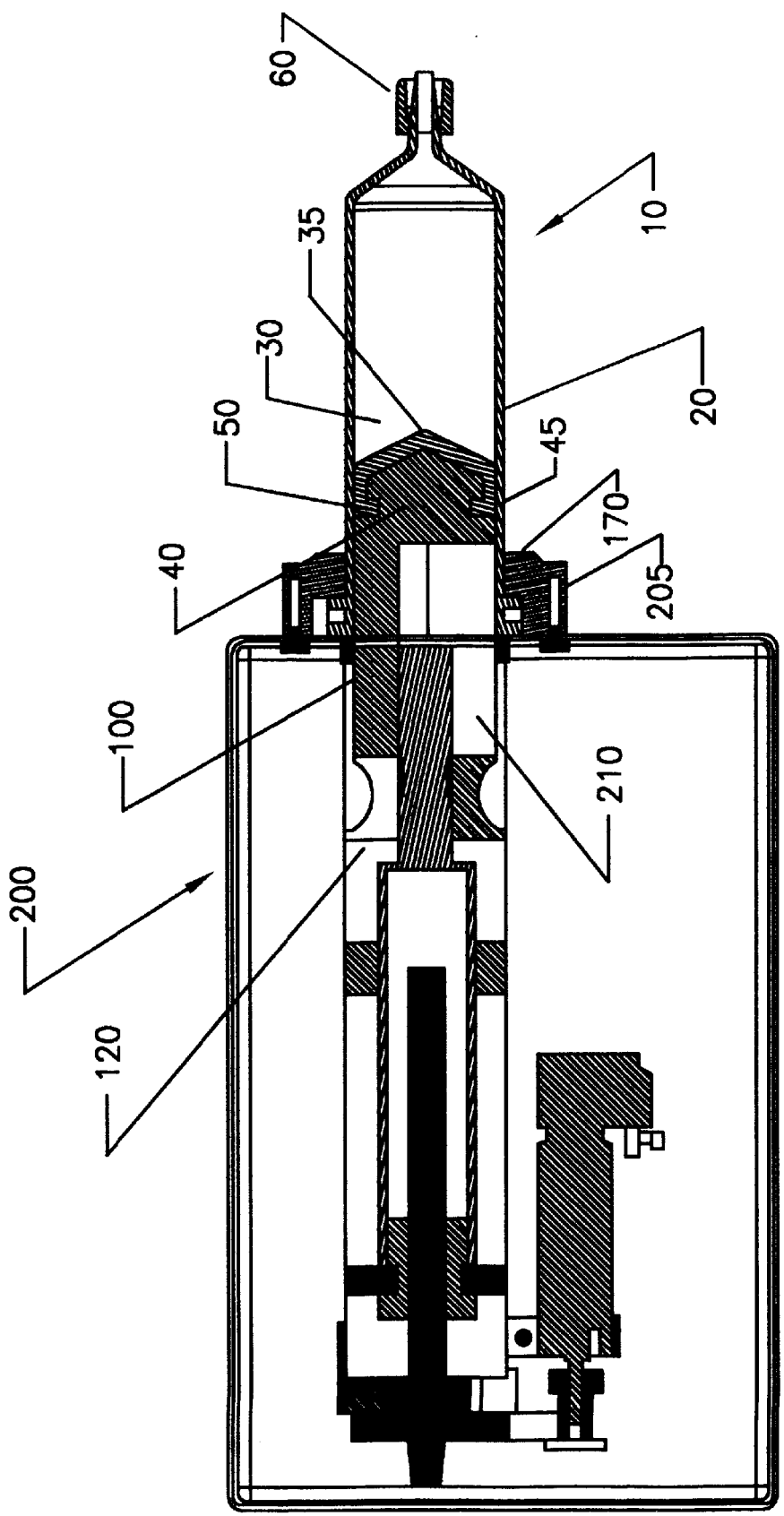
FIG. 3D illustrates a cross-sectional view of the powered injector of FIG. 3A connected to the syringe of FIG. 1.

As shown in FIG. 3C, injector housing 235 encloses a reciprocating drive member or piston member 210 which cooperates with syringe plunger extension 100 and, thereby, plunger 30 to inject an injection fluid from the interior of elongated cylindrical body 20 into a patient. Piston member 210 is extendible and retractable via a powered means preferably contained within injection housing 235 and comprising, for example, a motor or hydraulic system, including appropriate gearing (not shown). Injector housing 235 also preferably includes a motor controller for controlling operation of a motor and thereby controlling operation of piston member 210.

FIG. 3A shows that injector housing 235 preferably comprises a retainer 205 formed with an opening 230 therein for releasable mounting syringe 10 in a predetermined position relative to injector housing 235. Opening 230 formed in retainer 205 and syringe 10 preferably comprise cooperating mounting mechanisms for securely affixing syringe 10 to injector housing 235. Preferably, such cooperating mounting mechanisms comprise cooperating retaining flanges formed upon opening 230 and mounting flanges formed upon the rearward portion of syringe 10.

In a preferred embodiment, opening 230 comprises a pair of opposed, axially extending slots 250 and 255. Slots 250 and 255 preferably separate and define a pair of radially inwardly projecting syringe retaining flanges 260 and 265 formed around the circumference of opening 230. To the rear of retaining flanges 260 and 265 is a circumferential groove or channel 270, which is in communication with the axial slots 250 and 255. Retaining flanges 260 and 265 are preferably formed as a portion of retainer 205 of injector housing 235.

Figure 3E:
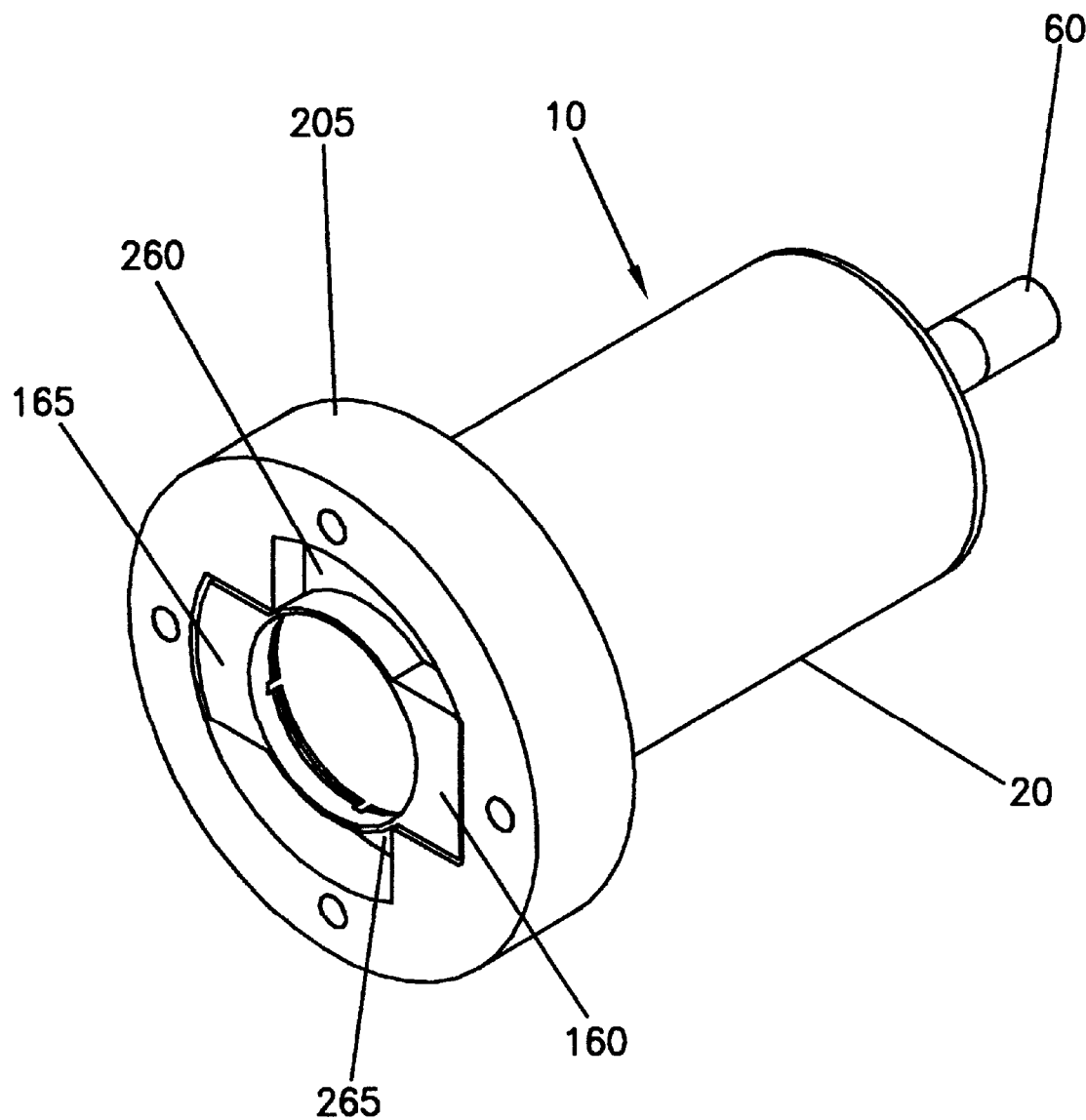
FIG. 3E illustrates a rear perspective view of an embodiment of a retainer in which a syringe has been partially mounted.
Figure 4A:
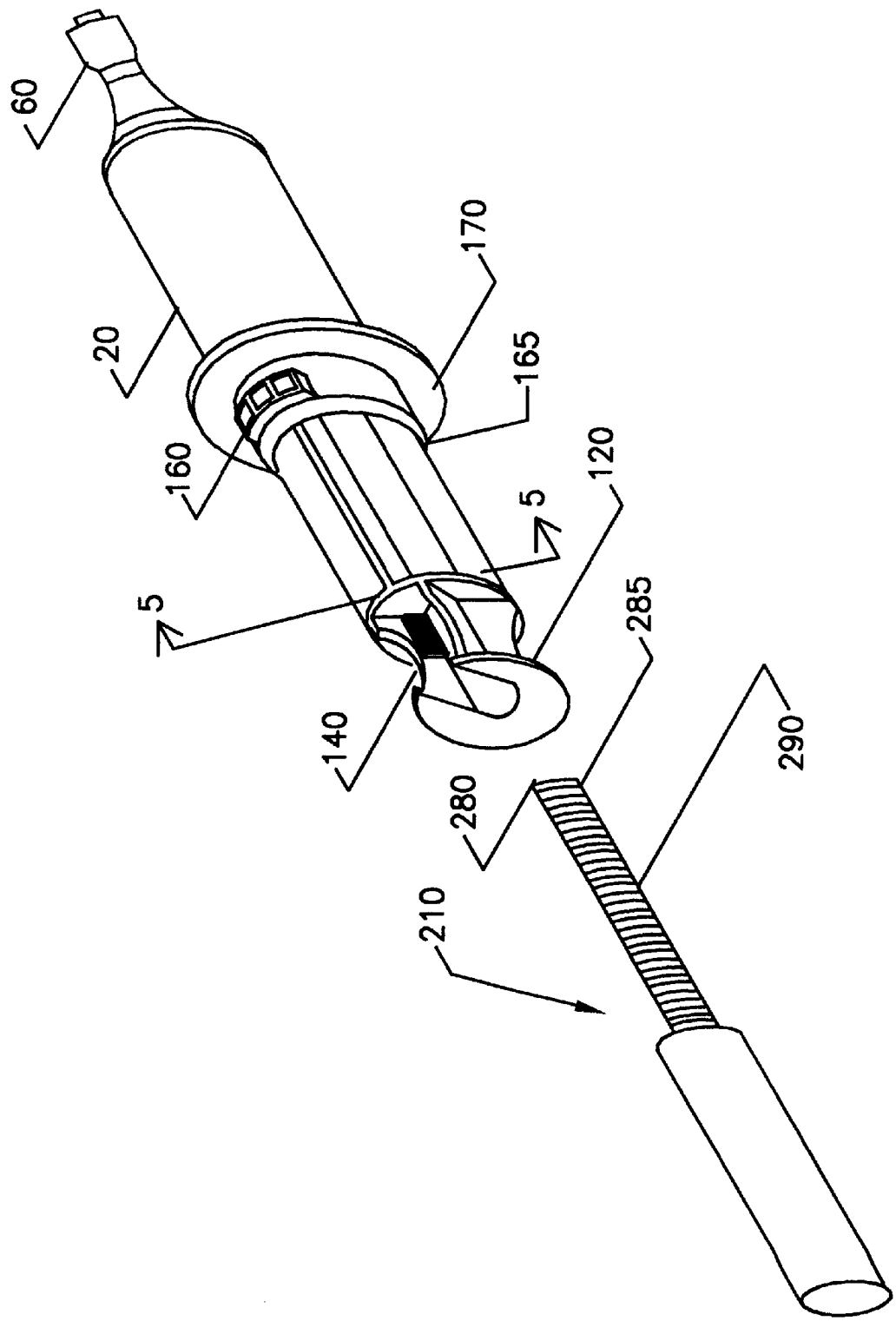
FIG. 4A illustrates proper alignment of an embodiment of a plunger extension and an embodiment of a piston member to effect a releasable connection therebetween.
Figure 5:
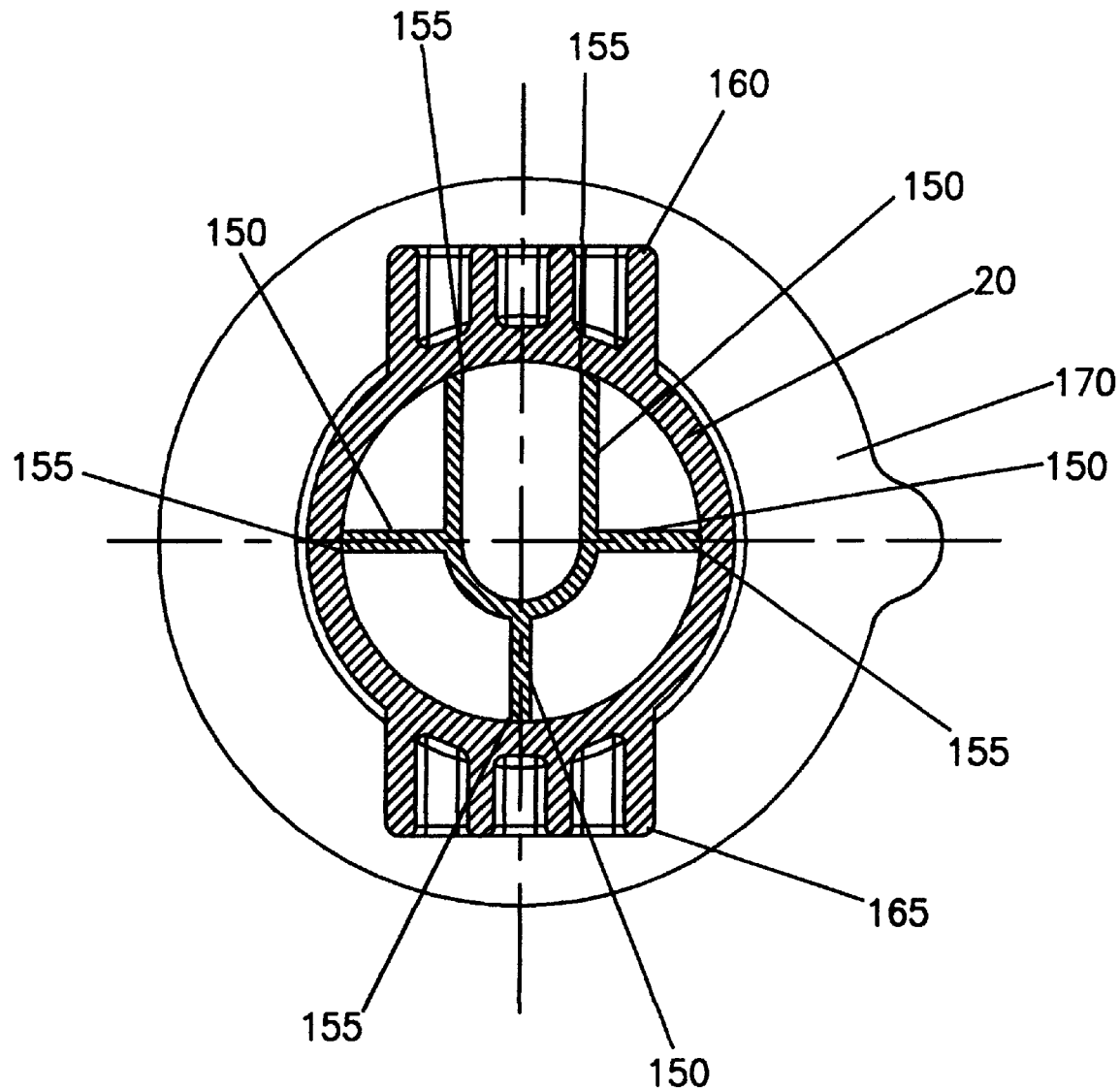
FIG. 5 illustrates a cross-sectional view of a syringe taken along line 5—5 of FIG. 4A.

Opening 230 may, for example, be machined out of aluminum or other suitable material such as plastic. Opening 230 receives and firmly secures syringe 10 to injector housing 235. In that regard, as shown in FIG. 4A, syringe 10 preferably comprises on a rear portion thereof a set of radially extending mounting flanges 160 and 165. As shown in FIGS. 3E and 5, mounting flanges 160 and 165 may be of a different shape to insure a particular alignment of syringe 10 when syringe 10 is mounted onto retainer 205. In this embodiment, slots 250 and 255 are shaped so as to receive their respective mounting flanges 160 and 165. It is understood, however, that mounting flanges 160 and 165, and their respective slots 250 and 255 may be of the same shape. A radially extending drip flange 170 is preferably formed forwardly from mounting flanges 160 and 165.

Drip flange 170 assists in proper axial positioning of syringe 10 with respect to the front wall of injector housing 235 by preferably abutting the face of the front wall when syringe 10 is properly positioned. Drip flange 170 further substantially prevents liquid from leaking into injector housing 235, which may cause damage to injector 200. Drip flange 170 also provides structural reinforcement for elongated cylindrical body 20.

Figure 3F:
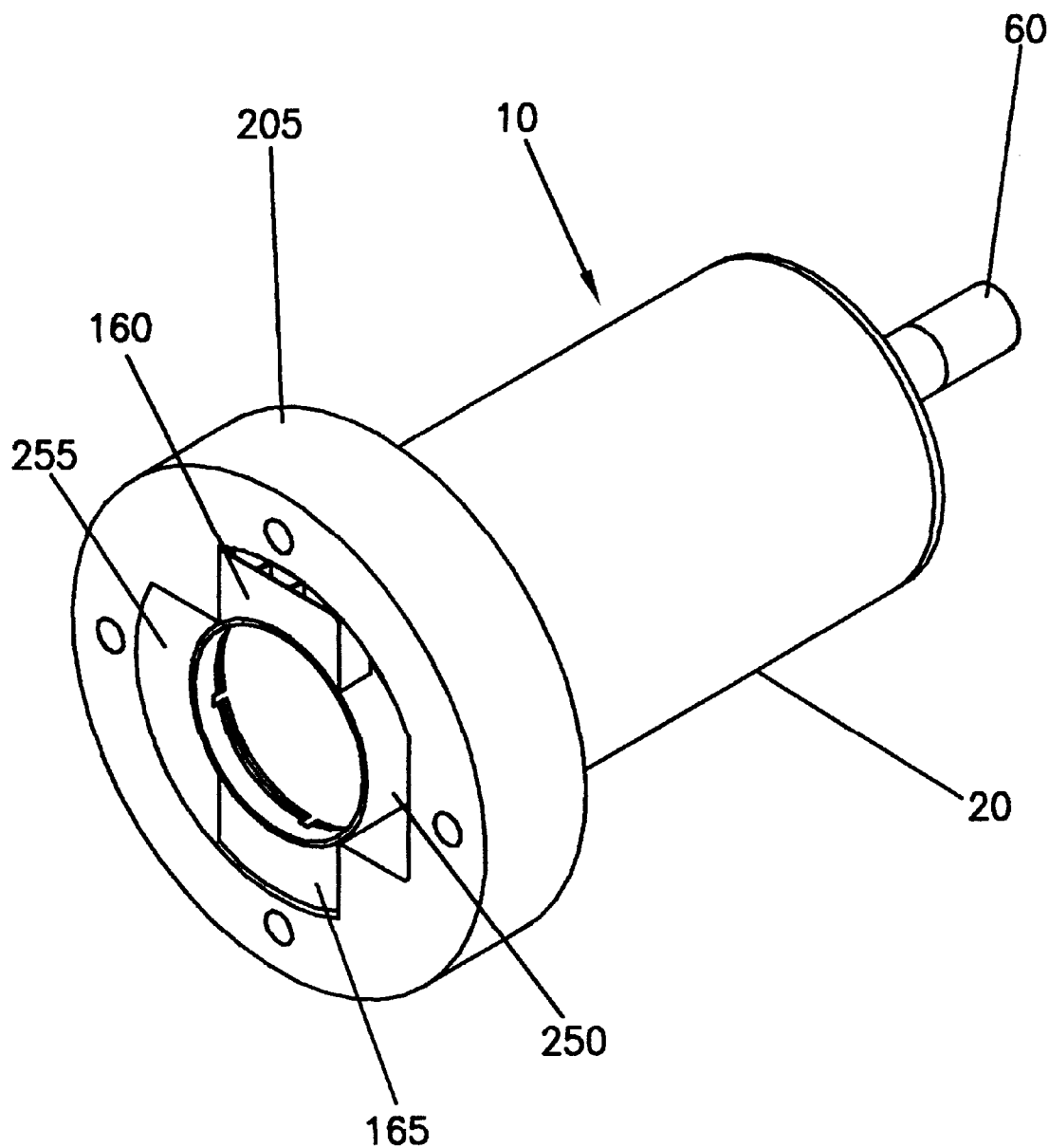
FIG. 3F illustrates a rear perspective view of the retainer of FIG. 3E in which the syringe has been rotated 90 degrees for secure mounting.

During mounting of syringe 10 in injector housing 235, mounting flanges 160 and 165 pass through slots 250 and 255, respectively, until, for example, drip flange 170 abuts face 280 of retainer 205. When syringe 10 is mounted on the injector front wall as described above, drip flange 170 preferably makes a sealing engagement with face 280. Syringe 10 and mounting flanges 160 and 165 are then rotated from the position illustrated in FIG. 3E to the position illustrated in FIG. 3F such that mounting flanges 160 and 165 are rotatably and closely received in a circumferential channel 270. In this position, mounting flanges 160 and 165 abut and are retained by retaining flanges 260 and 265, respectively. The mounting procedure is simply reversed to dismount syringe 10 from injector 200.

Figure 2B:
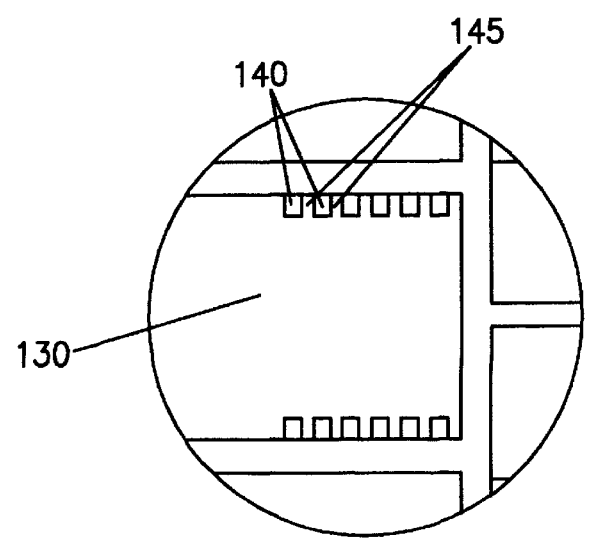
FIG. 2B illustrates an exploded view of a portion of the plunger base and plunger extension of FIG. 2A comprising cooperating attachment members for releasably connecting to a piston member.
Figure 2C:
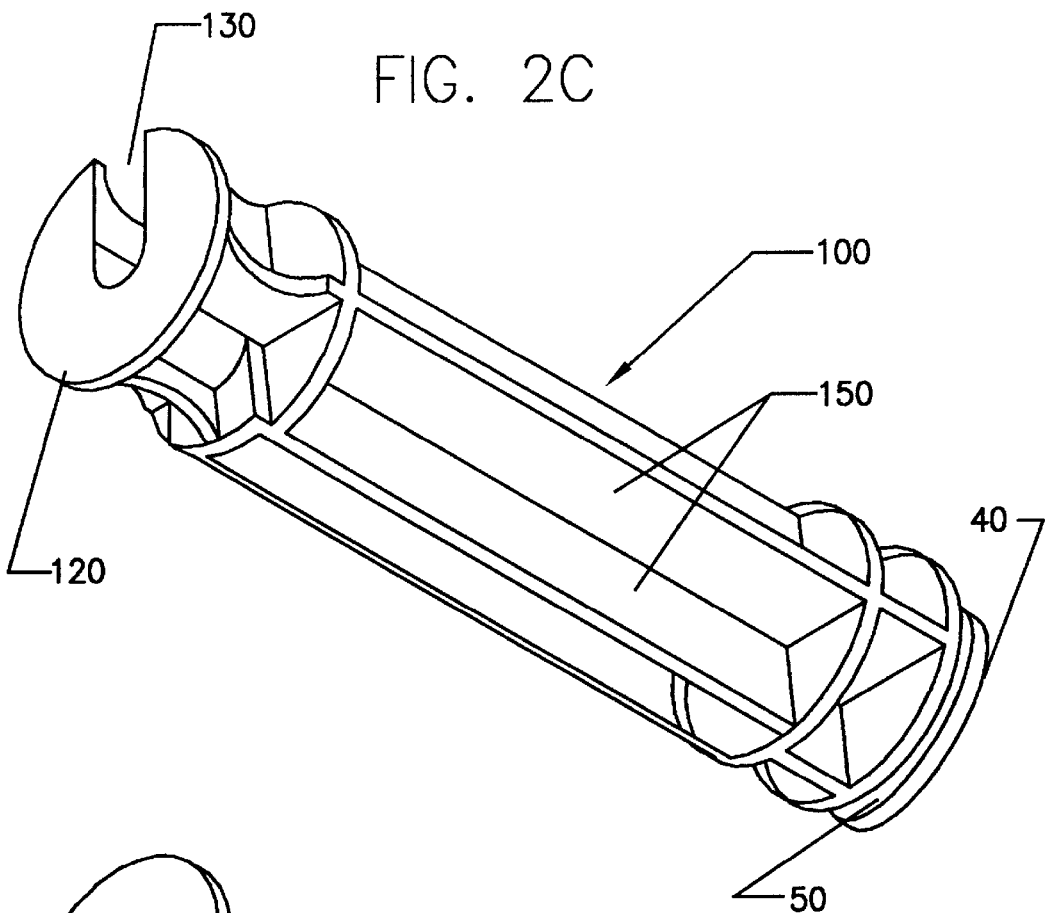
FIG. 2C illustrates a top perspective view of the embodiment of the plunger base and plunger extension of FIG. 2A.
Figure 2D:
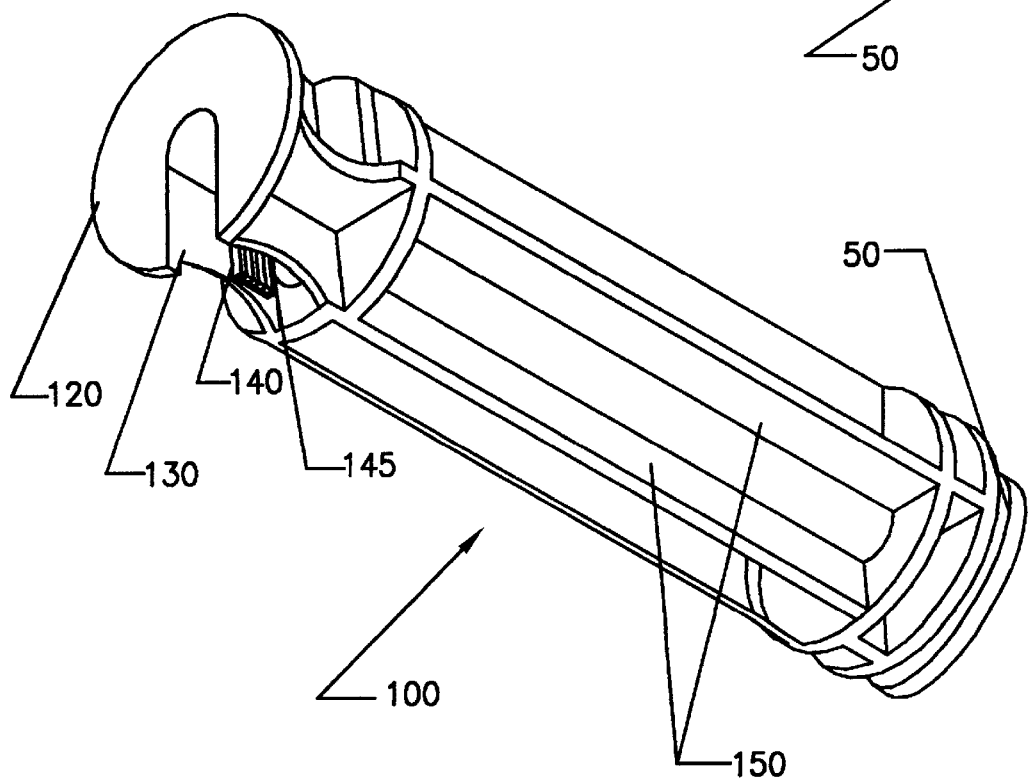
FIG. 2D illustrates a bottom perspective view of the embodiment of the plunger base and plunger extension of FIG. 2A.

Plunger extension 100 preferably comprises means for releasably attaching plunger extension 100 to piston member 210 of powered injector 200. As described above, piston member 210 cooperates with plunger extension 100 to impart substantially linear, reciprocal motion to plunger 30. In one embodiment, as shown in FIGS. 2A and 2B, plunger extension 100 preferably comprises a passage 130 through rear pressure member 120 and extending through a portion of plunger extension 100. Passage 130 preferably comprises two opposing rows of radially inwardly extending flanges or ridges 140 and intermediate grooves 145 symmetrically positioned over a range of axial positions on the sidewalls thereof. Flanges 140 and intermediate grooves 145 mate with two opposing rows of cooperating radially outwardly extending flanges or ridges 280 and intermediate grooves 285 positioned over a range of axial positions on drive member 210 to create a readily releasable attachment of plunger extension 100 and piston member 210 over a range of axial positions of the plunger 30.

Figure 4B:
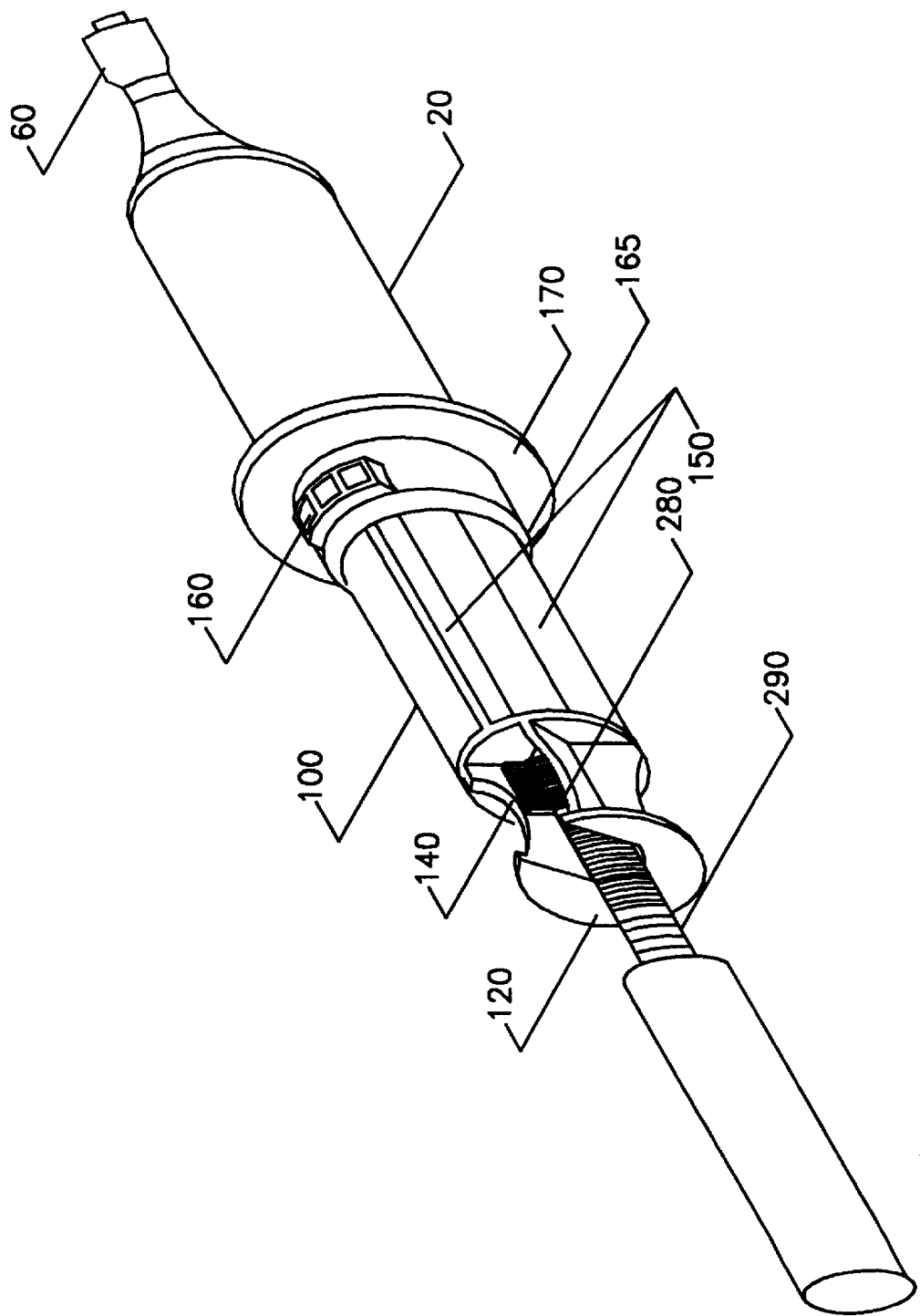
FIG. 4B illustrates insertion of the piston member within a passage in the plunger extension.

In this embodiment, piston member 210 preferably comprises two symmetrically formed and substantially flat sides 290 and 295 (best illustrated in FIGS. 4D and 4E) and two curved portion therebetween on which flanges 280 and intermediate grooves 285 are formed. Passage 130 is preferably shaped in the form of an arch. In this embodiment, plunger extension 100 and piston member 210 are rotated to the relative positions illustrated in FIG. 4A such that substantially flat sides 290 and 295 are aligned to face flanges 140 of passage 130. In this position, piston member 210 is substantially freely slidable in and out of passage 130. As illustrated in FIG. 4B, plunger extension 100 and piston member 210 are moved in a linear manner relative to each other such that piston member 210 enters passage 130 and that flanges 140 and grooves 145 are aligned with corresponding grooves 285 and flanges 280, respectively.

Figure 4C:
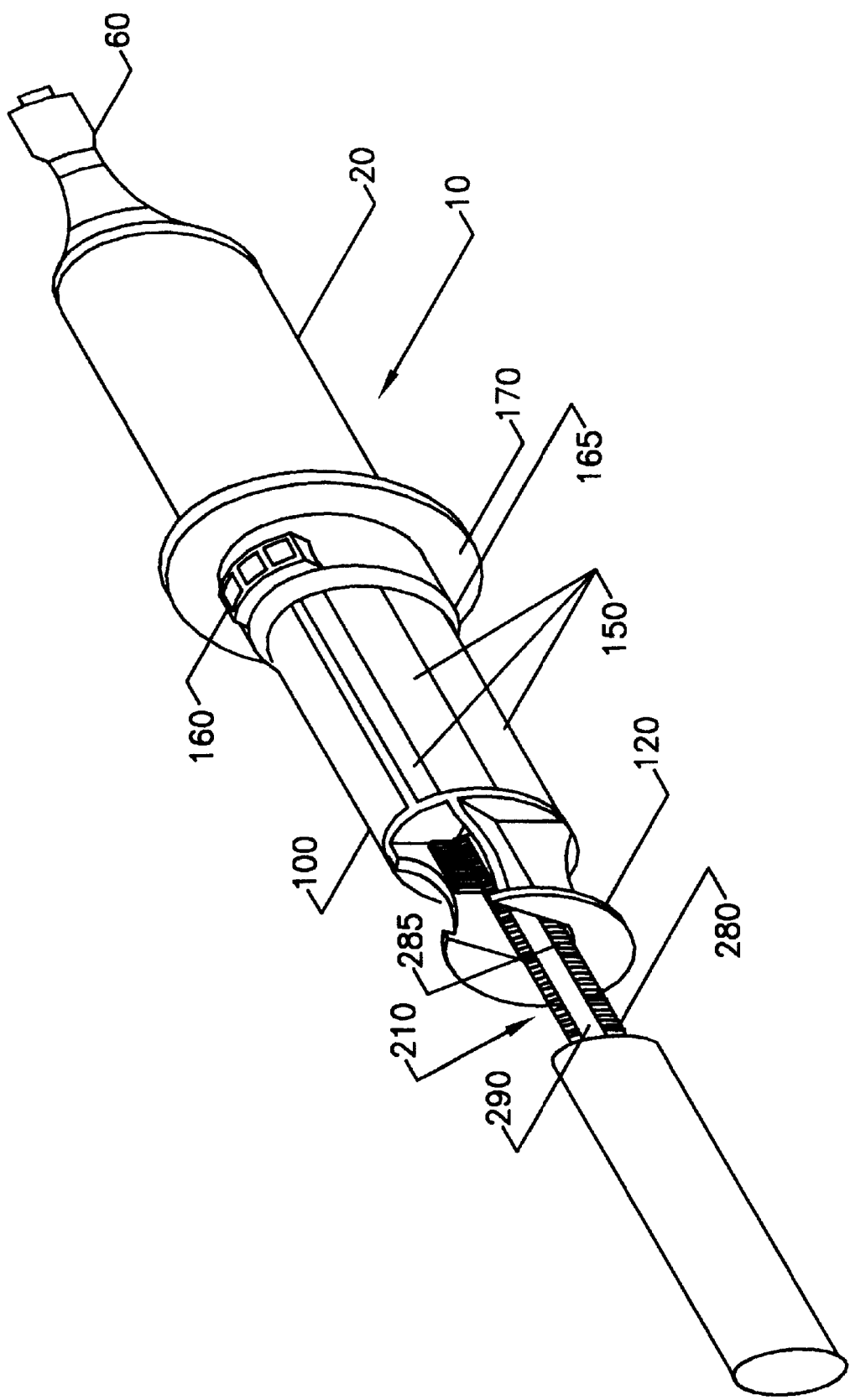
FIG. 4C illustrates rotation of the plunger extension of FIG. 4B relative to the piston member to releasably connect the plunger extension to the piston member.
Figure 4D:
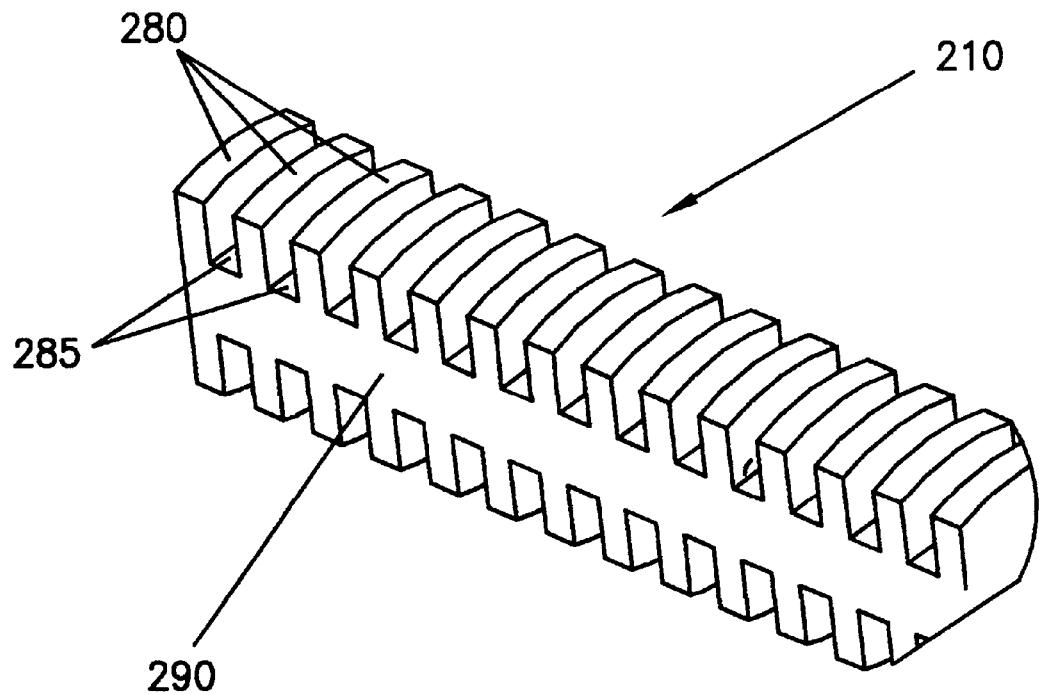
FIG. 4D illustrates an exploded view of the piston member.
Figure 4E:
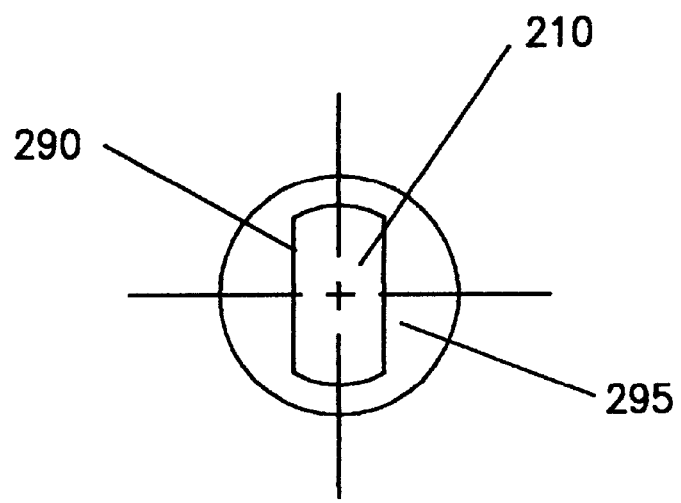
FIG. 4E illustrates a front view of the piston member.

Upon achieving such alignment, plunger extension 100 and piston member 210 are preferably rotated relative to each other such that a plurality of flanges 280 mate with a plurality of grooves 145 and a plurality of flanges 140 mate with a plurality of grooves 285 to create a secure connection between piston member 210 and plunger extension 100 as illustrated in FIG. 4C. In this position, piston member 210 can impart powered forward or rearward motion to plunger 30. To detach plunger extension 100 from piston member 210, plunger extension 100 and piston member 210 are rotated relative to each other such that ridges 140 face substantially flat sides 290 and 295. In this position, as set forth above, plunger extension 100 and drive member 210 are easily slidable relative to each other and may be separated.

Each of flanges 140 and cooperating flanges 280 are preferably positioned relatively close to adjacent flanges 140 and 280, respectively, to facilitated connection. There is also preferably some amount of "play" in the system to allow proper alignment of corresponding flanges and grooves upon rotatable attachment of plunger extension 100 to drive member 210. For example, plunger 30 may move forward or rearward a small amount during connective rotation to allow proper alignment. Preferably, flanges 140 and flanges 280 have tapered leads to assist in assuring proper alignment.

Preferably, rotation of mounting flanges 160 and 165 of the syringe 10 to seat in circumferential channel 270 also results in attachment of plunger extension 100 and drive member 210 as described above. Thus, the plunger extension 100 and drive member 210 need not be manually aligned, as required by prior art syringe/injector systems. The degree of rotation required for mounting syringe 10 upon injector housing 235 and the degree of rotation required to releasably connect plunger extension 100 to piston member 210 may, for example, each be approximately 90 degrees.

In this embodiment, syringe 10 is preferably fabricated such that upon inserting plunger 30 and the attached plunger extension 100 within elongated cylindrical body 20, plunger extension 100 cannot be easily rotated relative to elongated cylindrical body 20. In this manner, elongated cylindrical body 20 and plunger extension 100 preferably can be rotated as a unit. In the embodiment illustrated in FIG. 5, this result is accomplished via spines 150 on plunger extension 100 which cooperate with slots 155 on elongated cylindrical body 20 to substantially prevent relative rotation between plunger extension 100 and elongated cylindrical body 20, while permitting reciprocal axial motion of the plunger extension 100 within cylindrical body 20.

Figure 7:
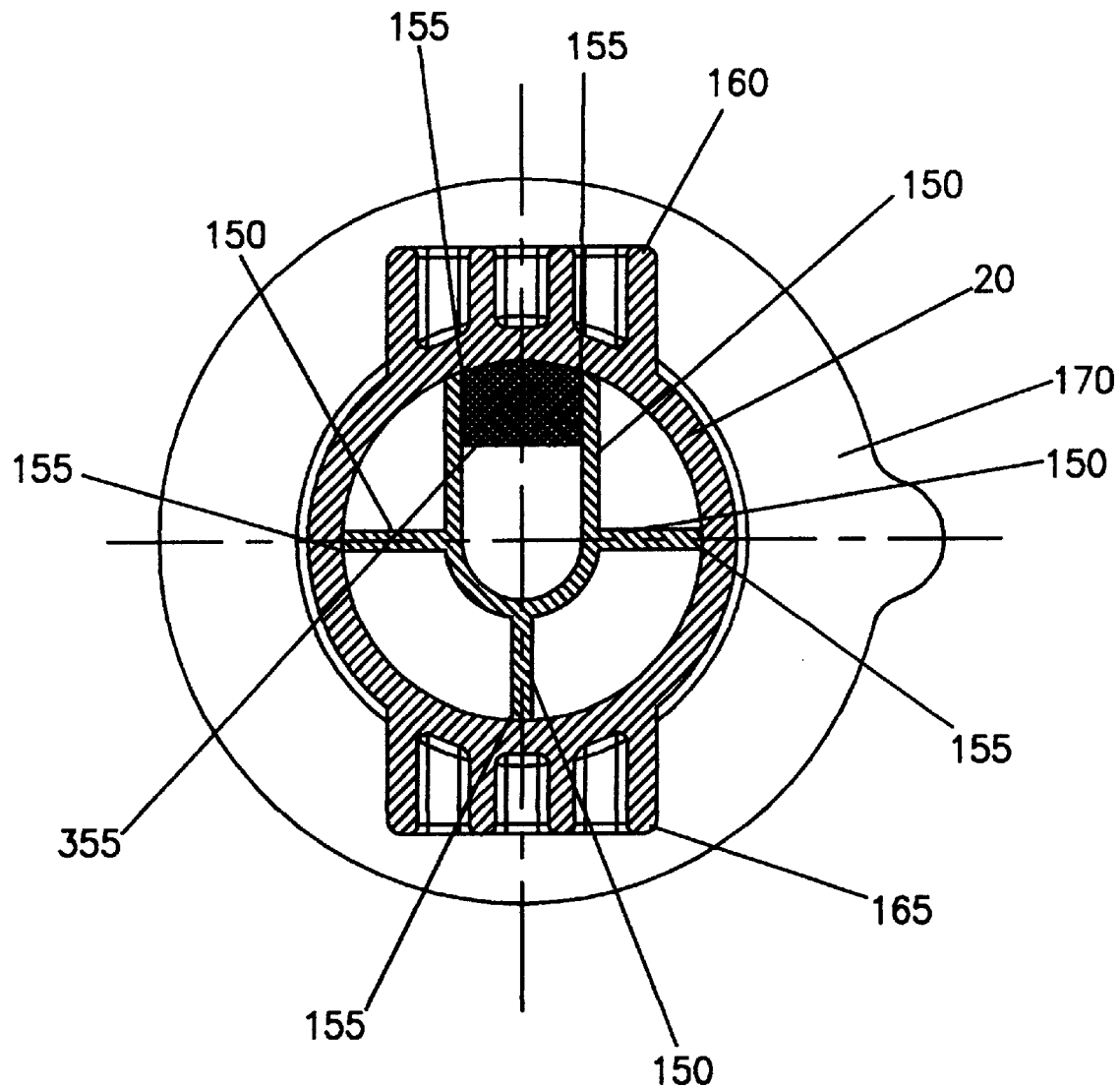
FIG. 7 illustrates a cross-sectional view of another embodiment of a syringe taken along line 5—5 of FIG. 4A.

As shown in FIG. 7, instead of or in addition to slots 155 formed in the elongated body 20, one or more tab members 355 may extend from the interior surface of the elongated body 20 to engage the spines 150 and thereby prevent relative rotation between the plunger extension 100 and the elongated body 20. Preferably, as shown in FIG. 7, at least one tab member 355 extends between two adjacent spine members 150 to prevent plunger extension 100 rotation. Further, the tab members 355 may be attached to or integrally formed with the elongated body 20.

Likewise, the rotation of mounting flanges 160 and 165 to align flanges 160 and 165 with slots 250 and 255 to remove or dismount syringe 10 from injector housing 235 preferably results in detachable alignment of plunger extension 100 from piston member 210. In this manner, syringe 10 can be easily removed from injector housing 235.

Figure 6:
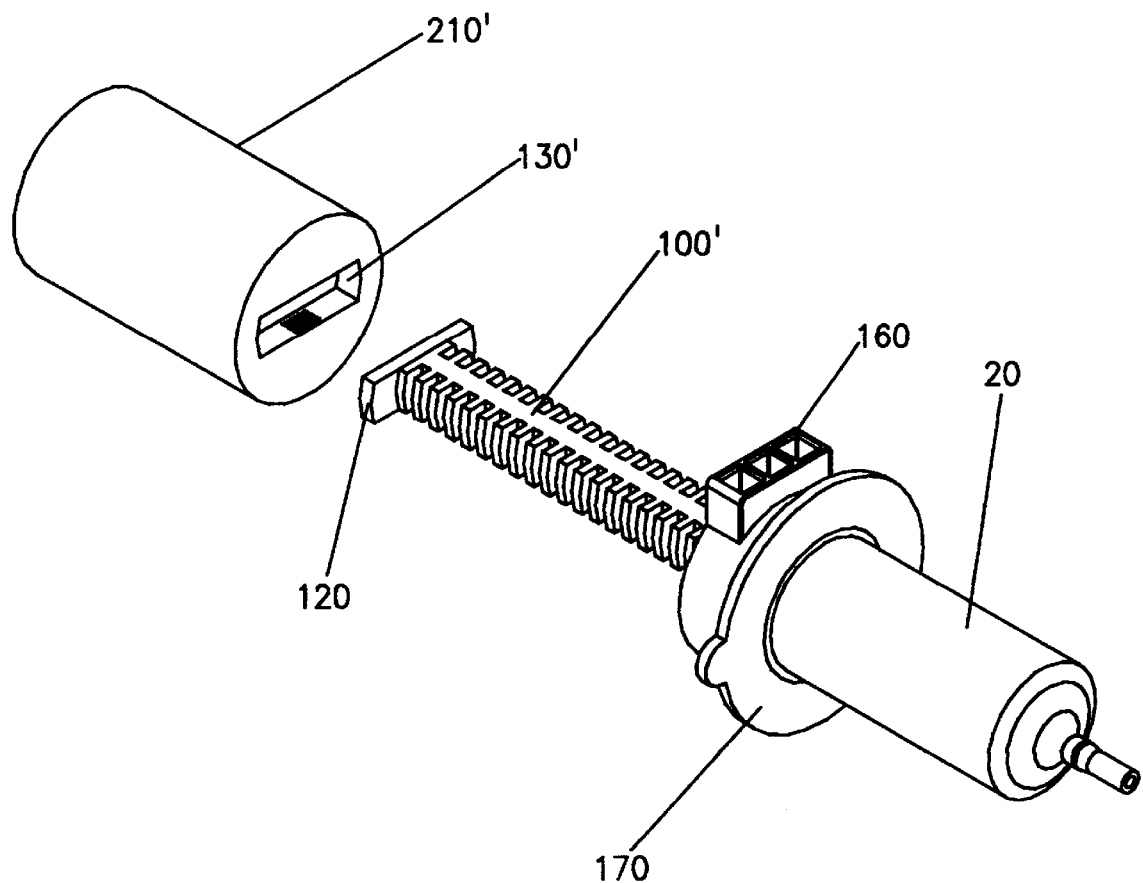
FIG. 6 illustrates a perspective view of another embodiment of a plunger extension and drive member.

In an alternative to the embodiment, as shown in FIG. 6, the plunger extension 100' extending from the rear of plunger 30 can comprise a grooved rod similar to drive member 210 illustrated in FIGS. 4A through 4D. In this embodiment, the drive member 210' of the injector preferably comprises a passage 130' therethrough similar to passage 130 formed in the plunger extension 100. Each of the drive member 210' and the plunger extension 100' once again preferably comprises a plurality of cooperating attachment members (for example, circumferential flanges and intermediate grooves or channels) located over a range of axial positions thereon. The plunger extension 100' of this embodiment passes through the passage 130' of the drive member 210' to allow releasable connection of the drive member 210' to the plunger extension 100'.

The extension of the plunger extension of the present invention beyond the rear of elongated cylindrical body 20, enables operation of syringe 10 in a manual mode. That is, by application of appropriate manual force to plunger extension 100, for example, a user can draw fluid into elongated cylindrical body 20 or expel fluid from elongated cylindrical body 20. Plunger extension 100 is preferably of sufficient length that the user may take advantage of a maximum volume of elongated cylindrical body 20. Plunger extension 100 also preferably includes a flange or pressure member 120 on the rearward end thereof to facilitate manual operation.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A syringe for use with a powered injector comprising a drive member having at least one injector attachment member, the syringe comprising:

an elongated body comprising at least one engagement member defining a slot on an interior surface thereof; and a plunger movably mounted in the elongated body for pressurizing a fluid medium, the plunger comprising at least one spine member operable to engage the at least one engagement member on the interior surface of the elongated body and a plurality of plunger attachment members located over a range of axial positions on the plunger, one or more of the plunger attachment members operable to releasably engage the at least one injector attachment member on the drive member upon rotation of the plunger with respect to the drive member, the at least one spine member and the at least one engagement member cooperable to prevent relative rotation between the plunger and the elongated body.

2. The syringe of claim 1 wherein the at least one engagement member comprises at least one tab member extending from the interior surface of the elongated body.

3. The syringe of claim 2 wherein the at least one tab member is integrally formed with the elongated body.

4. The syringe of claim 2 wherein the at least one spine member comprises two spine members, and further wherein the at least one tab member extends between the two spine members.

5. The syringe of claim 1 wherein the at least one spine member and the at least one engagement member allow the plunger to axially move within the elongated body.

6. A syringe for use with an injector having a drive member, the syringe comprising:

an elongated body comprising at least one engagement member defining a slot on an interior surface thereof; and a plunger movably mounted in the elongated body for pressurizing a fluid medium, the plunger comprising at least one spine member operable to engage the at least one engagement member on the interior surface of the elongated body and at least one plunger attachment member operable to releasably engage one or more of a plurality of injector attachment members located over a range of axial positions on the drive member upon rotation of the plunger with respect to the drive member, the at least one spine member and the at least one engagement member cooperable to prevent relative rotation between the plunger and the elongated body.

7. The syringe of claim 6 wherein the at least one engagement member comprises at least one tab member extending from the interior surface of the elongated body.

8. The syringe of claim 7 wherein the at least one tab member is integrally formed with the elongated body.

9. The syringe of claim 7 wherein the at least one spine member comprises two spine members, and further wherein the at least one tab member extends between the two spine members.

10. The syringe of claim 6 wherein the at least one spine member and the at least one engagement member allow the plunger to axially move within the elongated body.

11. An injection system comprising, in combination, an injector and a syringe, the injector comprising:

a housing; and a drive member disposed within the housing, the drive member comprising a plurality of injector attachment members located over a range ot axial positions thereon; the syringe comprising:

an elongated body comprising at least one engagement member defining a slot on an interior surface thereof; and a plunger movably disposed in the elongated body for pressurizing a fluid medium, the plunger comprising at least one spine member operable to engage the at least one engagement member on the interior surface of the elongated body and a plurality of plunger attachment members located over a range of axial positions thereon, one or more of the plunger attachment members operable to releasably engage one or more of the injector attachment members upon rotation of the plunger with respect to the drive member, the at least one spine member and the at least one engagement member cooperable to prevent relative rotation between the plunger and the elongated body.

12. The injection system of claim 11 wherein the at least one engagement member comprises at least one tab member extending from the interior surface of the elongated body.

13. The injection system of claim 12 wherein the at least one tab member is integrally formed with the elongated body.

14. The injection system of claim 12 wherein the at least one spine member comprises two spine members, and further wherein the at least one tab member extends between the two spine members.

15. The injection system of claim 11 wherein the at least one spine member and the at least one engagement member allow the plunger to axially move within the elongated body.

* * * * *